(12) United States Patent
Shah

(10) Patent No.: US 9,835,527 B2
(45) Date of Patent: Dec. 5, 2017

(54) TISSUE PROCESSING REAGENT

(71) Applicant: Sakura Finetek U.S.A., Inc., Torrance, CA (US)

(72) Inventor: Amit D. Shah, Torrance, CA (US)

(73) Assignee: SAKURA FINETEK U.S.A., INC., Torrance, CA (US)

( * ) Notice: Subject to any disclaimer, the term of this patent is extended or adjusted under 35 U.S.C. 154(b) by 0 days.

(21) Appl. No.: 14/984,946

(22) Filed: Dec. 30, 2015

(65) Prior Publication Data

US 2017/0191907 A1  Jul. 6, 2017

(51) Int. Cl.
  *G01N 1/30*  (2006.01)

(52) U.S. Cl.
  CPC ......... *G01N 1/30* (2013.01); *G01N 2001/305* (2013.01)

(58) Field of Classification Search
  CPC ................................ C12Q 1/6806; G01N 1/30
  See application file for complete search history.

(56) References Cited

U.S. PATENT DOCUMENTS

| | | | |
|---|---|---|---|
| 5,422,277 A | 6/1995 | Connelly et al. | |
| 5,849,517 A | 12/1998 | Ryan | |
| 5,976,829 A | 11/1999 | Birnboim | |
| 6,017,725 A | 1/2000 | Hoffmann et al. | |
| 6,177,514 B1 * | 1/2001 | Pathak | A61L 27/3604 514/16.5 |
| 6,337,189 B1 | 1/2002 | Ryan | |
| 6,458,322 B1 | 10/2002 | Harris | |
| 6,531,317 B2 | 3/2003 | Guirguis et al. | |
| 2009/0053704 A1 * | 2/2009 | Novoradovskaya | C12Q 1/6806 435/6.18 |
| 2014/0186882 A1 | 7/2014 | Berberich et al. | |
| 2015/0050652 A1 | 2/2015 | Madau et al. | |
| 2016/0003716 A1 | 1/2016 | Torres et al. | |

FOREIGN PATENT DOCUMENTS

WO  WO-9319209  9/1993

OTHER PUBLICATIONS

Cooper, 1924, p. 948-950.*
Dapson, R. W., "Glyoxal fixation: how it works and why it only occasionally needs antigen retrieval", Biotechnic & Histochemistry, vol. 82, No. 3, (Jan. 1, 2007), 161-166.
Sakura Finetek U.S.A., Inc., "Extended European Search Report", EP Application No. 16204884.7, (May 17, 2017).
Andrews, B. A. K., "1,3,-Dioxolane, An Alternative to Formalin as a Standard for Formaldehyde", Textile Research Journal, USDA, ARS, Southern Regional Research Center, New Orleans, Louisiana 70179, U.S.A., (Dec. 1987), 705-710.
Dalpozzo, R. , et al., "Er(OTf)3 as a Mild Cleaving Agents for Acetals and Ketals", Synthesis 2004(4): 496-498, vol. 4, (2004), 496-498.
Dalpozzo, R. , et al., "Simple and Efficient Chemoselective Mild Deprotection of Acetals and Ketals Using Cerium(III) Triflate", American Chemical Society, J. Org. Chem., 67, (Nov. 15, 2002), 9093-9095.
Gregg, B. T., et al., "Indium(III) Triflouromethanesulfonate as an Efficient Catalyst for the Deprotection of Acetals and Ketals", American Chemical Society, J. Org. Chem. 2007, 72, (Jun. 27, 2007), 5890-5893.
Sun, J. , et al., "Highly Efficient Chemoselective Deprotection of O,O-Acetals and O,O-Ketals Catalyzed by Molecular Iodine and Acetone", American Chemical Society, J. Org. Chem. 2004, 69, (Nov. 12, 2004), 8932-8934.

* cited by examiner

*Primary Examiner* — Bin Shen
(74) *Attorney, Agent, or Firm* — Blakely Sokoloff Taylor & Zafman; Tom Babbitt

(57) ABSTRACT

A method including treating a biological sample taken from a body with a composition including an acetal solvent. A method including contacting a fixed biological sample taken from a body with a composition including an acetal solvent as at least one a dehydrating, clearing and infiltration process.

24 Claims, No Drawings

TISSUE PROCESSING REAGENT

FIELD

Tissue processing.

BACKGROUND

Tissues from the body taken for diagnosis of disease processes are often processed in the histology laboratory to produce thin tissue sections which can be mounted on slides and viewed under a microscope by a pathologist for analysis. These pre-analytical processes generally include, in order, gross examination fixation, dehydration, clearing, paraffin infiltration and embedding. The procedure is used for processing tissues including biopsies, larger specimens removed at surgery, or tissues from autopsy.

Gross examination generally consists of describing the macroscopic specimen and placing all or selected parts of it into a small plastic cassette which holds the tissue while it is being processed to a paraffin block. Initially, the cassettes are placed into a fixative.

Following gross examination, a tissue is fixated. A purpose of fixation is to preserve tissues permanently in as life-like a state as possible by altering structures of proteins such that degradation by autolysis does not occur. A variety of fixatives are available for use, depending on the type of tissue present and features to be demonstrated. Major groups of fixatives, classified according to mechanism of action include aldehydes, mercurials, alcohols, oxidizing agents and picrates. Formalin fixation is best carried around neutral pH, for example, in the range of 6-8. Hypoxia of tissues tends to lower the pH, so there should be buffering capacity in the fixative to prevent excessive acidity. Common buffers include phosphate, bicarbonate, malate, cacodylate, and veronal. Commercial formalin, for example, may be buffered with phosphate at a pH of 7. Penetration of tissues depends upon the diffusability of each individual fixative. One way to improve penetration of a fixative is to gross (cut) the tissue thinly (2 to 3 millimeters (mm)). Penetration into a thin tissue section will occur more rapidly than for a thick section. The volume of fixative is generally important with a 10:1 ratio or greater of fixative to tissue typically targeted. Agitation of the specimen in a fixative will often also enhance fixation.

Once the tissue has been fixed or fixated, the tissue needs to be processed into a form in which it can be made into thin sections for microscopic examination. The usual way this is done is with paraffin. Tissues embedded in paraffin, which provides a solid support matrix for the tissue, allowing it be sectioned at a thickness on the order of 2 to 20 microns. Getting fixed tissue into paraffin for sectioning is called tissue processing with the main steps in this process being dehydration, clearing, infiltration and embedding.

Tissues fixed in aqueous solutions cannot be directly infiltrated with paraffin. First, the water from the tissues must be removed by dehydration. This may be done with a series of alcohols at different concentrations (e.g., 70 percent to 95 percent to 100 percent). Alternatively, the dehydration is done with a mixture of formalin and alcohol. Other dehydrants can also be used such as acetone or mixtures of different solvents.

Following dehydration, the tissue is cleared. "Clearing" consists of removal of the dehydrant and some of the lipids with a substance that will be miscible with the embedding medium (e.g., paraffin). The most common clearing agent is xylene.

Once cleared, the tissue is infiltrated with an embedding agent such as paraffin. Finally, the tissue in a cassette or removed from its cassette is placed into molten paraffin and then the paraffin is cooled to form a solidified block embedding or encapsulating the tissue so that it can be sectioned. Alternatively, the tissue can be processed in a sectionable cassette, embedded in paraffin along with the cassette and sectioned. Once the tissue has been embedded in a solid paraffin block, the tissue can be cut into sections that can be placed on a slide. This is done with a microtome. Once sections are cut, they are floated on a warm water bath that helps remove any wrinkles. The tissue sections in paraffin are then picked up from the water bath and placed on a glass microscope slide.

DETAILED DESCRIPTION

In one embodiment, a composition including an acetal solvent is disclosed that is operable or suitable for treating a biological sample taken from a body. A biological sample such as a tissue taken from the body for diagnosis or research includes but is not limited to, a biopsy, a specimen removed at surgery and/or tissues from autopsy. Also disclosed is a method including treating a biological sample taken from a body for diagnosis with a composition including an acetal. Treating a biological sample in this regard, in one embodiment, is focused on a pre-analytical process such as fixation, clearing and/or embedding of the biological sample for subsequent examination/diagnosis.

Representative acetals suitable for a composition for treating a biological sample include methylal, ethaylal, butylal, dioxolane, glycerol formal, acetaldehyde diethyl acetal and mixtures thereof. Dioxolane is one particular preferred acetal solvent. A dioxolane as described herein includes 1,3-dioxolane as well as its adducts and mixtures thereof. Such adducts include, but are not limited, to 2-methyl-1,3-dioxolane; 4-methyl-1,3-dioxolane; 2,2-dimethyl-1,3-dioxolane; 2-methyl-1,3-dioxolane; 4-methyl-2-phenyl-1,3-dioxolane (benzaldehyde propylene glycol), 1,2-dioxolane and adducts thereof. 1,3-dioxolane is one particular preferred dioxolane due to its favorable toxicity profile and commercial availability.

In one embodiment, a composition including a dioxolane is used in a process in the histology laboratory to produce microscopic slides that can be viewed under a microscope for analysis. In one embodiment, a composition including a dioxolane can be used as a dehydrating agent alone or in combination with, for example, an alcohol, acetone, xylene or glycol (separately or as a mixture). In another embodiment, the composition including a dioxolane can be used alone or in combination with an alcohol (separately or as a mixture) as a dehydration agent after a fixation process. Still further, a composition including a dioxolane can be used in an infiltration process with, for example, an additive such as paraffin to improve infiltration of the paraffin in the tissue.

As a clearing agent, a composition including a dioxolane may be used at a concentration of 100 percent (e.g., 100 percent dioxolane composition) or may be combined with another clearing agent or agents such as hydrocarbon clearing agents (e.g., xylene, hexane, mineral oil), hydrocarbon clearing agents with oxygen-based functional groups (e.g., alcohols (e.g., ethanol), acetates, ethers, acetals, etc.) or mixtures of clearing agents at a lower composition (e.g., 70 percent to 85 percent of a dioxolane with the remainder another clearing agent or agents).

The following are example uses of a composition including a dioxolane in pre-analytical processes to treat a tissue taken from a body for diagnosis.
1. The use of a dehydrating reagent such as ethanol, methanol, isopropanol, acetone etc. or combinations of such reagents to achieve dehydration of the tissues followed by use of a dioxolane as an independent reagent or as a mixture with other reagents such as ethanol, xylene, etc. for clearing. Specific examples include:
   a) the use of 95 to 100 percent ethanol for dehydration followed by the use of 1,3-dioxolane for clearing;
   b) the use of an ethanol-isopropyl alcohol mixture (70:30v/v) for dehydration followed by the use of 1,3-dioxolane for clearing;
   c) the use of acetone-isopropyl alcohol-ethylene glycol mixture for dehydration followed by the use of 1,3-dioxolane for clearing;
   d) the use of 70 percent reagent ethanol (absolute ethanol denatured with 1 to 10 percent isopropanol and methanol) for dehydration followed by the use of 1,3-dioxolane for clearing; and
   e) the use of 95 to 100 percent reagent ethanol with up to 2 percent acetic acid followed by the use of 1,3-dioxolane for clearing.
2. The use of a 1,3-dioxolane-reagent ethanol mixture (e.g., 80:20, 85:15, 90:10, 95:5 v/v) for clearing.
3. The use of a dioxolane as a part of a dehydrating mixture to achieve tissue dehydration and again using the dioxolane to achieve clearing as either a standalone clearing reagent or as a part of a clearing mixture such as those listed above. Representative mixtures for dehydration include reagent ethanol (e.g., ethanol) 1,3-dioxolane mixture (70:30; 50:50 and 30:70 v/v).
4. The use of a dioxolane as an additive in paraffin wax (e.g., up to 20 percent dioxolane in paraffin) to facilitate infiltration of the wax into the tissue.

A composition including a dioxolane for a dehydrating, clearing or infiltration process may be used on conventional tissue processors for conventional processing protocols that generally are several hours long or for short protocols of lesser time (e.g., 60 minutes or less). A composition including a dioxolane can also be used in such processes on conventional tissue processors for processing protocols executed at elevated temperatures up to 70° C. reagent processing temperature. For example, a composition including a dioxolane with reagent alcohol for tissue dehydration and alone or as part of a mixture for clearing may be performed at operating temperatures with no added heat to the processing or at elevated reagent temperatures of 60° C. For infiltration processes, a composition including a dioxolane may be combined with paraffin at a temperature on the order of 65-70° C.

A composition including a dioxolane for use as a dehydrating agent, a clearing agent or an infiltration agent is also suitable with microwave assisted tissue processing for general processing protocols of about 60 minutes for regular sized tissues and shorter time periods for smaller tissues (biopsy, core, etc.)

EXAMPLES

The following represent specific examples of a use of a composition including a dioxolane in pre-analytic processing.

Example 1

Tissues were grossed and fixed in 10 percent neutral buffered formalin for 6 to 24 hours. The tissues were then placed in reagent alcohol (90-100 percent) for 30 minutes. The tissues were then placed in 1,3-dioxolane for 40 minutes, with microwave processing. Finally, the tissues were infiltrated by placement in paraffin mixed with 1,3-dioxolane (5 percent v/v) at about 65° C. for 40 minutes.

Example 2

Tissues were grossed and fixed in 10 percent neutral buffered formalin for 6 to 24 hours. The tissues were then placed in two consecutive reagent alcohol (95-100 percent) stations for 15 minutes each (or one reagent alcohol station for 30 minutes). The tissues were then placed in two consecutive 1,3-dioxolane stations for 15 minutes each. Finally, the tissues were infiltrated by placement in two consecutive paraffin (65° C.) stations for 15 minutes each.

Example 3

Tissues were grossed and fixed in 10 percent neutral buffered formalin for 6 to 24 hours. The tissues were then placed in two consecutive reagent alcohol (95-100 percent) stations for 30 minutes each (or one reagent alcohol station for 30-60 minutes). The tissues were then placed in two consecutive 1,3-dioxolane stations for 30 minutes each. Finally, the tissues were infiltrated by placement in two consecutive paraffin (65° C.) stations for 30 minutes each.

Example 4

In this example, the processing protocol of Example 2 was followed and the processing was done by microwave assist for the 1,3-dioxolane step and paraffin steps.

Implementations

Implementation 1 is a method including treating a biological sample taken from a body with a composition including an acetal solvent.

In Implementation 2, the acetal solvent of the method of Implementation 1 includes a dioxolane.

In Implementation 3, prior to treating the biological sample with the composition, the method of Implementation 1 or 2 includes fixing the biological sample.

In Implementation 4, after fixing the biological sample, the method of Implementation 3 includes dehydrating and clearing the biological sample and treating the biological sample with the composition includes treating as at least a part of at least one dehydrating and clearing.

In Implementation 5, prior to treating the biological sample with the composition, the method of Implementation 4 includes dehydrating the fixed biological sample.

In Implementation 6, dehydrating of the method of Implementation 5 includes treating the fixed biological sample with a dehydrating composition including an alcohol.

In Implementation 7, the dehydrating composition of the method of Implementation 5 includes at least one of acetone and a glycol.

In Implementation 8, dehydrating of the method of Implementation 4 includes treating the fixed biological sample with a dehydrating composition including the composition.

In Implementation 9, after fixing the biological sample, the method includes dehydrating, clearing the biological sample and infiltrating the biological tissue, and treating the biological sample with the composition of the method of any of Implementations 1-3 includes treating as at least a part of infiltrating the biological tissue.

In Implementation 10, the composition of the method of Implementation 6 further includes paraffin.

In Implementation 11, the dioxolane of the method of Implementation 2 includes 1,3-dioxolane.

Implementation 12 is a method including contacting a fixed biological sample taken from a body with a composition including an acetal solvent as at least one a dehydrating, clearing and infiltration process.

In Implementation 13, the acetal solvent of the method of Implementation 12 includes a dioxolane.

In Implementation 14, the dioxolane of the method of Implementation 13 includes 1,3-dioxolane.

In Implementation 15, the process of the method of any of Implementations 12-14 is a clearing process.

In Implementation 16, the method of Implementation 15 further includes contacting the biological sample with another clearing agent.

In Implementation 17, another clearing agent of the method of Implementation 16 includes at least one of a hydrocarbon clearing agent and a hydrocarbon clearing agent with an oxygen-based functional group.

In Implementation 18, the dioxolane and another clearing agent of the method of Implementation 16 include a mixture.

In Implementation 19, the process of the method of any of Implementations 12-14 is a dehydrating process.

In Implementation 20, the method of Implementation 19 further includes contacting the biological sample with an alcohol.

In Implementation 21, the acetal solvent and the alcohol of the method of Implementation 20 include a mixture.

In Implementation 22, the process of the method of Implementation 12 is an infiltration process.

In Implementation 23, the method of Implementation 22 further includes contacting the biological sample with a paraffin wax.

In Implementation 24, the dioxolane and paraffin of the method of Implementation 23 include a mixture.

In Implementation 25, a fixed biological sample such as a tissue sample made by the method of any of Implementations 1-24.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
    treating a biological sample taken from a body with a composition comprising an acetal solvent; and
    after treating the biological sample, containing the biological sample with a paraffin.

2. The method of claim 1, wherein the acetal solvent comprises a dioxolane.

3. The method of claim 2, wherein the dioxolane comprises 1,3-dioxolane.

4. The method of claim 1, wherein prior to treating the biological sample with the composition, the method comprises fixing the biological sample.

5. The method of claim 4, wherein after fixing the biological sample, the method comprises dehydrating, clearing and infiltrating the biological sample, and treating the biological sample with the composition comprises treating as at least a part of infiltrating the biological tissue.

6. The method of claim 5, wherein the composition further comprises a paraffin.

7. The method of claim 4, wherein after fixing the biological sample, the method comprises dehydrating and clearing the biological sample and treating the biological sample with the composition comprises treating as at least a part of at least one of dehydrating and clearing.

8. The method of claim 7, wherein dehydrating comprises treating the fixed biological sample with a dehydrating composition comprising the composition.

9. The method of claim 7, wherein prior to treating the biological sample with the composition, the method comprises dehydrating the fixed biological sample.

10. The method of claim 9, wherein dehydrating comprises treating the fixed biological sample with a dehydrating composition comprising an alcohol.

11. The method of claim 9, wherein the dehydrating composition comprises at least one of acetone and a glycol.

12. A method comprising:
    treating a fixed biological sample taken from a body to a dehydrating process, a clearing process and an infiltration process, wherein at least one of the dehydrating process, the clearing process and the infiltration process comprises contacting the fixed biological sample with a composition comprising an acetal solvent and wherein the infiltration process comprises infiltrating the fixed biological sample with an embedding agent.

13. The method of claim 12, wherein the acetal solvent comprises a dioxolane.

14. The method of claim 13, wherein the dioxolane comprises 1,3-dioxolane.

15. The method of claim 12, wherein the clearing process comprises contacting the fixed biological sample with a composition comprising an acetal solvent.

16. The method of claim 15, wherein the clearing process further comprises contacting the biological sample with another clearing agent.

17. The method of claim 16, wherein the another clearing agent comprises at least one of a hydrocarbon clearing agent and a hydrocarbon clearing agent with an oxygen-based functional group.

18. The method of claim 16, wherein the acetal solvent comprises a dioxolane and the acetal solvent and the another clearing agent comprise a mixture.

19. The method of claim 12, wherein the dehydrating process comprises contacting the fixed biological sample with a composition comprising an acetal solvent.

20. The method of claim 12, wherein the dehydrating process further comprises contacting the biological sample with an alcohol.

21. The method of claim 20, wherein the acetal solvent and the alcohol comprise a mixture.

22. The method of claim 12, wherein the infiltration process comprises contacting the fixed biological sample with a composition comprising an acetal solvent.

23. The method of claim 22, wherein the embedding agent comprises a paraffin.

24. The method of claim 22, wherein the dioxolane and the embedding agent comprise a mixture.

\* \* \* \* \*